United States Patent [19]

Small, Jr.

[11] 4,362,636

[45] Dec. 7, 1982

[54] CRANKCASE LUBRICANT AND METHOD FOR IMPROVING FUEL ECONOMY OF INTERNAL COMBUSTION ENGINES UTILIZING SAME

[75] Inventor: Vernon R. Small, Jr., Rodeo, Calif.

[73] Assignee: Chevron Research Company, San Francisco, Calif.

[21] Appl. No.: 215,954

[22] Filed: Dec. 12, 1980

[51] Int. Cl.$^3$ .............................................. C10M 1/26
[52] U.S. Cl. ............................. 252/56 R; 252/32.7 E
[58] Field of Search ...................................... 252/56 R

[56] References Cited

U.S. PATENT DOCUMENTS

| | | | |
|---|---|---|---|
| 2,204,601 | 6/1940 | Kavanagh et al. | 252/56 R X |
| 3,429,820 | 2/1969 | Lyons et al. | 252/56 R X |
| 3,626,559 | 12/1971 | Rossman et al. | 252/56 R X |

*Primary Examiner*—Andrew Metz
*Attorney, Agent, or Firm*—D. A. Newell; J. M. Whitney; V. J. Cavalieri

[57] ABSTRACT

Lubricating oils containing oil soluble hydroxyalkyl alkanoates have been found to reduce fuel consumption in an internal combustion engine.

8 Claims, No Drawings

CRANKCASE LUBRICANT AND METHOD FOR IMPROVING FUEL ECONOMY OF INTERNAL COMBUSTION ENGINES UTILIZING SAME

FIELD OF THE INVENTION

This invention relates to lubricating oil compositions and their use in reducing fuel consumption in internal combustion engines. More particularly, it deals with crankcase lubricating oil compositions containing 1,2 or 2,1-hydroxyalkyl alkanoates.

BACKGROUND OF THE INVENTION

With the crisis associated with diminishing amounts of fossil fuel and the rapidly increasing prices for this fuel, there has been a great deal of interest in reducing the amount of fuel consumed by automobile engines, and the like.

Thus, there is a great need to find lubricants that reduce the overall friction in the engine, thus reducing the energy requirements thereto.

U.S. Pat. No. 4,201,684 teaches lubricating oils containing sulfurized fatty acid amides, esters or esteramides of alkoxylated amines, which reduce friction between sliding metal surfaces in internal combustion engines.

U.S. Pat. No. 4,167,486 teaches lubricating oils containing certain acid esters having double bonds or the dimer or trimer of such acid esters. Reductions in fuel consumption in an internal combustion engine are claimed by using the lubricating oils in the crankcase of the engine.

So far as is known, no effort has been made to place lubricating oils containing the hydroxyalkyl alkanoates of this invention in the crankcase of an internal combustion engine.

U.S. Pat. No. 3,649,538 teaches a process for lubricating aluminum in an aluminum-shaping operation with a lubricant comprising a mineral oil and 0.1% to 30% by volume of a $C_{10}$–$C_{30}$ 1,2-diol.

SUMMARY OF THE INVENTION

According to the present invention, lubricating oils are provided which reduce friction between sliding metal surfaces in the crankcase of internal combustion engines. The reduced friction results from the addition to the lubricating oil of small amounts of hydroxyalkyl alkanoates of the formula:

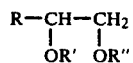

I wherein R is alkyl containing from 4 to 28 carbon atoms, and one of R' and R" is hydrogen and the other is alkanoyl containing 1 to 30 carbon atoms, or mixtures thereof.

Further, in accordance with the invention, there is provided a method for reducing fuel consumption in an internal combustion engine by treating the moving surfaces thereof with a composition comprising a major amount of a lubricant containing a fuel-reducing amount of the hydroxyalkyl alkanoates of the Formula I, or mixtures thereof.

DETAILED DESCRIPTION

The hydroxyalkyl alkanoates of the Formula I useful in the present invention are those having a total of from 7 to 60 carbon atoms, namely, from 6 to 30 carbon atoms in the hydroxyalkyl portion and from 1 to 30 carbon atoms in the alkanoyl portion.

Representative of the alkyl groups containing 4 to 28 carbon atoms defined by R include butyl, hexyl, octyl, decyl, dodecyl, pentadecyl, eicosyl, and the like. Preferably, the alkyl group contains from 8 to 18 carbon atoms, and most preferably, from 13 to 18 carbon atoms.

The alkanoyl groups containing 1 to 30 carbon atoms in the definition of R' and R" are derived from the corresponding alkanoic acids. Representative of the alkanoic acids, which include both saturated and unsaturated acids, and containing 1 to 30 carbon atoms from which the alkanol group is derived include formic acid, acetic acid, butanoic acid, hexenoic acid, octanoic acid, dodecanoic acid, oleic acid, eicosanoic acid, tricontanoic acid, and the like. Preferably, the alkanoyl group contains from 1 to 18 carbon atoms, and most preferably, 1 carbon atom.

Single carbon number species may be employed such as 2-hydroxydecyl octanoate, 2-hydroxyoctadecyl formate, 2-hydroxydodecyl dodecanoate, 2-hydroxyeicosyl formate and 1-methyloltetradecyl formate, and the like, but a blend of several carbon numbers is preferred. Typical blends include the mixture of about equal parts of 2-hydroxydecyl formate, 2-hydroxyundecyl formate, 2-hydroxydodecyl formate, 2-hydroxytridecyl formate, 2-hydroxytetradecyl formate, 2-hydroxypentadecyl formate, 2-hydroxyhexadecyl formate, 2-hydroxyheptadecyl formate, 2-hydroxyoctadecyl formate, 2-hydroxynonadecyl formate and 2-hydroxyeicosyl formate, or a mixture of 1-methylolundecyl formate, 1-methyloltridecyl formate, and 1-methylolpentadecyl formate, or a mixture of 1-methyloltetradecyl formate, 1-methylolpentadecyl formate, 1-methylolhexadecyl formate and 1-methylolheptadecyl formate, or a mixture of 2-hydroxytetracosyl formate, 2-hydroxyhexacosyl formate, and 2-hydroxyoctacosyl formate. The corresponding acetates, octanoates, octadecanoates, oleates, and the like may also be used in place of the formates.

The hydroxyalkyl alkanoates useful for this invention are readily prepared from the corresponding 1-olefin by methods well known in the art. For example, the olefin is first reacted with peracid, such as peroxyacetic acid or perbenzoic acid to form an alkane-1,2-epoxide which is readily converted to a 2-hydroxyalkyl alkanoate upon treatment with an alkanoic acid containing 1 to 30 carbon atoms. In yet another process, the olefin is first halogenated to a 1,2-dihaloalkane then hydrolyzed to an alkane-1,2-diol by reaction first with sodium acetate and then with sodium hydroxide, or the olefin is epoxidized as described above and readily hydrolyzed under acid or basic catalysis to the alkane-1,2-diol, and finally esterified with an equal molar amount of alkanoic acid containing 1 to 30 carbon atoms to give a mixture of 2-hydroxyalkyl alkanoate and 1-methylolalkyl alkanoate. Finally, a product predominating in 1-methylolalkyl alkanoates may be made by a series of steps in which an appropriate aldehyde is first reacted with 1,3-dithiacyclopentane under basic conditions to give the mercaptal of a 2-hydroxyaldehyde, which is converted to the corresponding mercaptal-ester by reaction with an appropriate alkanoic anhydride. This material is preferentially hydrolyzed to the aldehyde ester by treatment with methyl iodide, acetonitrile and water. Reduction of the aldehyde gives the desired 1-methylolalkyl alkanoate.

1-Olefins are available from the thermal cracking of waxes. This process produces olefins of all carbon numbers. 1-Olefins having an even number of carbon atoms, are prepared by the well-known ethylene "growth" reaction. Olefins obtained by either of these processes are essentially linear in structure with little or no branching. Linear olefins are the preferred olefins for conversion into hydroxyalkyl alkanoates of the Formula I.

The lubricating compositions used in the process of this invention contain a major amount of a lubricating oil and from about 0.1% to 5.0% by weight of the hydroxyalkyl alkanoates of the Formula I, preferably, from 0.5% to 4.0%, and most preferably, 1% to 2% by weight based on the weight of the total composition. The optimum amount of a hydroxyalkyl alkanoate within these ranges will vary slightly depending on the base oil and other additives present in the oil.

Additive concentrates are also included within the scope of this invention. In the concentrate additive form, the hydroxyalkyl alkanoate is present in a concentration ranging from 5% to 50% by weight.

The lubricating compositions are prepared by admixing, using conventional techniques, the appropriate amount of the desired hydroxyalkyl alkanoate with the lubricating oil. When concentrates are being prepared, the amount of hydrocarbon oil is limited, but is sufficient to dissolve the required amount of hydroxyalkyl alkanoate. Generally, the concentrate will have sufficient hydroxyalkyl alkanoate to permit subsequent dilution with 1- to 10-fold more lubricating oil.

The hydroxyalkyl alkanoates of the Formula I can be used in mineral oil or in synthetic oils of viscosity suitable for use in the crankcase of an internal combustion engine. Crankcase lubricating oils have a viscosity up to about 85 SUS at 210° F.

The addition of the hydroxyalkyl alkanoates to the lubricating oil as described above results in mileage benefits in both compression and spark ignition engines.

Crankcase lubricating oils of the present invention usually have a viscosity of up to about SAE 40. Sometimes such motor oils are given a classification at both 0° and 210° F., such as SAE 10W40 or SAE 5W30.

Mineral oil for use as the base oil in this invention includes paraffinic, naphthenic and other oils that are ordinarily used in the lubricating oil compositions.

The synthetic hydrocarbon oils include longchain alkanes such as cetanes and olefin polymers such as trimers and tetramers of octene and decene. The synthetic oils with which these can be mixed include (1) ester oils such as pentaerythritol esters of monocarboxylic acids having 2 to 20 carbon atoms, (2) polyglycol ethers, (3) polyacetals, and (4) siloxane fluids. Especially useful among the synthetic esters are those made from polycarboxylic acids and monohydric alcohols. More preferred are the ester fluids made from pentaerythritol, or mixtures thereof with di- and tripentaerythritol, and an aliphatic monocarboxylic acid containing from 1 to 20 carbon atoms, or mixtures of such acids.

Blends of mineral oil with synthetic oil are also useful. For example, blends of 10% to 25% by weight hydrogenated 1-decene trimer with 75% to 90% by weight 150 SUS (100° F.) mineral oil gives an excellent lubricant base.

The lubricating oils are usually compounded with a variety of additives. These additives include antioxidants, dispersants, rust inhibitors, detergents, foam inhibitors, basic metal compounds, corrosion inhibitors, anti-wear agents, viscosity index (VI) improvers, friction control agents, elastomer swell agents, extreme pressure (EP) agents, pour point depressants, and metal deactivators. All of these additives are well known in the lubricating oil art.

Preferably, the conventional formulated oil will contain dispersants such as alkenyl succinimides, detergents such as alkali or alkaline earth metal hydrocarbyl sulfonates or phenates, or combinations thereof as well as the overbased metal derivatives thereof, and extreme wear and anti-wear agents such as alkyl, aryl, alkaryl or aralkyl zinc dithiophosphates.

More particularly, with respect to the alkali or alkaline earth metal hydrocarbyl sulfonate, the hydrocarbyl group may be derived from a petroleum fraction, from a synthetically alkylated aromatic fraction, or from an aliphatic group such as polyisobutylene. Examples of these are sodium, calcium, magnesium or barium salts of sulfonated petroleum fractions or of polyisobutylene which has been sulfonated. These compositions are well known in the art and include both neutral and overbased sulfonates having base numbers of up to about 400 or more. In an ordinary formulation, they would be used in an amount to provide from 10 to 300 mmols/kg of alkaline earth metal and preferably, from 10 to 60 mmols/kg.

The phenate for use in this invention can be any one of those additives conventionally used in lubricating oil formulations which are alkali or alkaline earth metal salts of aromatic phenols ordinarily alkylated aromatic phenols wherein the alkylating group has from about 9 to about 30 carbon atoms. The phenol may be mono or dialkylated. Preferable salts are calcium, magnesium or barium salts. The phenates may be sulfurized and may also be neutral or overbased having base numbers of up to 400 or more. These phenates are usually used in amounts to provide 10 to 300 mmols/kg alkali or alkaline earth metal and more preferably, about 10 to 60 mmols/kg.

The zinc dialkyl dithiophosphates contains from 3 to 18 carbon atoms in each alkyl group. These compositions are well known in the art. Preferred alkyl groups contain from 6 to 12 carbon atoms although mixed zinc dialkyl dithiophosphates may also be used wherein one group contains 3 to 4 carbon atoms and the other group contains 6 to 12 carbon atoms. The aryl, alkaryl or aralkyl zinc dithiophosphates contain from about 6 to 30 carbon atoms. Preferred groups include phenyl, benzyl, octylphenyl, and tetrapropenyl-substituted phenyl, and the like.

The succinimide present in the formulation is an alkenyl succinimide prepared by reacting, for example, a polyisobutenyl succinic anhydride with a polyethylene polyamine such as tetraethylene pentaamine. The alkenyl substituent is preferably a polyisobutene group having a molecular weight from about 800 to 5,000. Succinimides of this type are described in U.S. Pat. Nos. 3,172,892 and 3,219,666, the disclosures of which are hereby incorporated by reference. The alkenyl succinimide can be reacted with boric acid or a similar boron-containing compound to form borated dispersants having utility in this invention. The borated succinimides are intended to be included within the scope of the term "alkenyl succinimide".

As mentioned above, other additives conventionally used in the art may be used with the formulation disclosed in this invention. The formulations used commercially are often multigrade oils. Multigrade oils are obtained by adding viscosity index improvers as is well known in the art. Typical viscosity index improvers include polyalkyl methacrylates or ethylene-propylene copolymers or styrene diene copolymers. It is also possible to use a dispersant VI improver.

The following examples are offered to specifically illustrate the development. It is to be understood they are illustrations only and that the invention shall not be limited except as limited by the appended claims.

EXAMPLE 1

To a 2-liter reaction flask was added 114 grams (0.5 mol) of a mixture comprising about equal parts by weight of $C_{15}$–$C_{18}$ alpha-olefins and 263 mls (5 mols) of 88% formic acid. The reaction mixture was heated to about 70° C. after which 226 mls of 15% $H_2O_2$ (1 mol) was added dropwise over a period of 5 hours. The reaction mixture was then stirred for an additional 44 hours at about 70° C. After cooling, the organic phase was separated and diluted with an equal volume of toluene, and stripped on a roto vac for ½ hour at 120° C. at 0.25 mm Hg. The mixture of $C_{15}$–$C_{18}$ 2-hydroxyalkyl formate obtained weighed 138.90 grams and had a hydroxyl No. of 121 mg KOH/gm.

In a similar fashion, a mixture of $C_{11}$–$C_{14}$ 2-hydroxyalkyl formates, as well as 2-hydroxydodecyl formate and 2-hydroxyoctadecyl formate are prepared by substituting the corresponding alpha-olefins for the $C_{15}$–$C_{18}$ alpha-olefins in the above example.

EXAMPLE 2

To a 2-liter reaction flask equipped with a reflux condenser and Dean Stark collector was charged 262 grams (1 mol) of $C_{15}$–$C_{18}$ 1,2-diol, 268 grams (0.95 mol) of oleic acid, 1 gram p-toluene sulfonic acid and 500 mls xylene. The reaction mixture was heated at reflux (155° C.) with stirring for 66 hours and 15 mls water was collected in the Dean Stark trap. The xylene was then evaporated and 517 grams of the product was collected. Infrared analysis of the product indicated a characteristic carbonyl bond at 1740 cm$^{-1}$.

EXAMPLE 3

Tests were carried out which demonstrate the improvements in fuel economy obtained by adding oil compositions containing the hydroxyalkyl alkanoates of this invention to the crankcase of an automobile engine.

In these tests, Ford 302 CID 2.3 liter engines were run under constant output conditions with lubricating oils with and without the hydroxyalkyl alkanoates.

The engines were run on dynamometers at conditions simulating 55 miles per hour under approximately road load. This test was repeated several times under constant conditions with the base oil and then several times with the same oil containing 2% by weight of the $C_{15-18}$ hydroxyalkyl formate of Example 1. The base oil was a typical commercial oil formulated for use in a crankcase. The oil compositions of this invention containing the hydroxyalkyl alkanoate was found to reduce fuel consumption of the engine an average of 2–3%.

The comparisons were made with fully formulated 10W-30 oil containing 3–5% of an alkenyl succinimide, 30 mmols/kg overbased magnesium hydrocarboyl sulfonate, 20 mmols/kg of overbased sulfurized calcium phenate, 18 mmols/kg dialkyl zinc dithiophosphate, and 5.5% of a polymethacrylate-based VI improver.

Also, formulated crankcase oils each containing 2% by weight of $C_{18-20}$ 2-hydroxyalkyl formate, 2-hydroxydecyl octadecanoate, 1-hydroxyoctadecyl formate, or a mixture of $C_{15-18}$ 2-hydroxyalkyl octadecanoate, or a mixture of $C_{15-18}$ 2-hydroxyalkyl oleate are also effective in reducing fuel consumption in an internal combustion engine.

What is claimed is:

1. In a lubricating oil formulated for use in the crankcase of an internal combustion engine, the improvement of including in said formulated oil about 0.10% to 5.0% by weight of at least one hydroxyalkyl alkanoate of the formula:

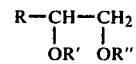

wherein R is alkyl containing from 4 to 28 carbon atoms, one of R' and R" is hydrogen and the other is alkanoyl containing 1 to 30 carbon atoms.

2. The composition of claim 1 wherein R contains from 8 to 18 carbon atoms and one of R' and R" contains from 1 to 18 carbon atoms.

3. The composition of claim 2 wherein R comprises a mixture of alkyl groups containing from 13 to 18 carbon atoms.

4. The composition of claim 1 wherein R is a mixture of $C_{13}$–$C_{16}$ alkyl groups and one of R' and R" is formyl or oleoyl and the other is hydrogen.

5. A method for reducing fuel consumption in an internal combustion engine by treating the moving surfaces thereof with a composition comprising a major amount of an oil of lubricating viscosity containing a fuel-reducing amount of at least one hydroxyalkyl alkanoate of the formula:

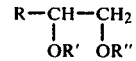

wherein R is alkyl containing from 4 to 28 carbon atoms, and one of R' and R" is hydrogen and the other is alkanoyl of 1 to 30 carbon atoms.

6. The method of claim 4 wherein R contains from 8 to 18 carbon atoms and one of R' and R" contains from 1 to 18 carbon atoms.

7. The method of claim 5 wherein R comprises a mixture of alkyl groups containing from 8 to 18 carbon atoms.

8. The method of claim 5 wherein R is a mixture of $C_{13}$–$C_{16}$ alkyl groups and one of R' and R" is formyl or oleoyl and the other is hydrogen.

* * * * *